United States Patent [19]

Dahl

[11] Patent Number: 5,537,289
[45] Date of Patent: Jul. 16, 1996

[54] WALL-MOUNTED MEDICAL MONITORING SYSTEM WITH REMOVABLE MODULES

[75] Inventor: James M. Dahl, Woodinville, Wash.

[73] Assignee: Spacelabs Medical, Inc., Redmond, Wash.

[21] Appl. No.: 209,641

[22] Filed: Mar. 11, 1994

[51] Int. Cl.⁶ ................................................. H05K 7/16
[52] U.S. Cl. ..................... 361/681; 364/708.1; 312/209
[58] Field of Search ................................. 361/680–686, 361/825, 829; 364/708.1; 52/36.1, 36.4, 36.5, 220.7, 220.8; 248/225.1, 920, 921; 312/209, 223.1, 107, 245; 211/190

[56] References Cited

U.S. PATENT DOCUMENTS

| | | | |
|---|---|---|---|
| 3,291,432 | 12/1966 | Lucasey | 248/278 |
| 4,662,524 | 5/1987 | Fullenkamp et al. | 211/190 |
| 4,715,385 | 12/1987 | Cudahy et al. | 128/710 |
| 4,727,934 | 3/1988 | Eckel et al. | 165/104.33 |
| 5,450,800 | 9/1995 | Leonard | 108/7 |

FOREIGN PATENT DOCUMENTS 0372863  6/1990  European Pat. Off. ....... A61M 5/142
0477551  4/1992  European Pat. Off. ....... A61G 12/00

*Primary Examiner*—Leo P. Picard
*Assistant Examiner*—Phuong T. Vu
*Attorney, Agent, or Firm*—Seed and Berry

[57] ABSTRACT

A medical monitoring system including a wall mounting plate to which a center support member is rigidly attached using a pair of mounting flanges which engage a pair of integral tracks on a forward surface of the mounting plate. The center support supports a plurality of module housings, each of which contains module slots for insertion of interchangeable modular components. A touch-screen display mounts to the center support member using a pedestal which permits rotation of the display in two orthogonal directions to permit ease of viewing by a user. An electronic device such as a power supply may be mounted to the tracks with mounting brackets to provide power for the monitoring system. A pair of secondary tracks on the mounting plate support a cable retainer and provide a passageway for cables to pass beneath the power supply where they are concealed from view.

14 Claims, 3 Drawing Sheets

5,537,289

WALL-MOUNTED MEDICAL MONITORING SYSTEM WITH REMOVABLE MODULES

TECHNICAL FIELD

The present invention relates to medical monitoring system, and more particularly, medical monitoring systems that are mounted on a wall or similar vertical structure.

BACKGROUND OF THE INVENTION

Medical monitoring systems typically include multiple electronic components, such as heart monitors, display screens, and power supplies. In some applications, however, the physical presence of the monitoring system components may obstruct access to people or things. For example, in some applications, monitoring system components with their accompanying cabling may impede access to a patient or block traffic flow through a confined area.

While some reduction of this obstruction may be achieved by positioning the components on fixed shelves or mobile cans, each of these approaches has significant drawbacks. Shelves extend outwardly from walls, blocking access even when no component is present. While this problem may be reduced by mounting the shelf high upon a wall, access to system components in such an elevated position may be difficult and cause delays in accessing and activating such components. In particular, in medical monitoring systems, such delays may cause delays in providing medical attention where time is of the essence. Moreover, where a visual display, such as a cathode ray tube ("CCRT") type of display, is used, the display may not be positionable upon the shelves for easy viewing. Additionally, because rear faces of the components abut walls when the components are placed on shelves, shelves provide limited access to connect and route cables to various components of monitoring systems.

Although medical monitoring system components mounted upon mobile cans may provide easier access to the components, such carts often block important walkways and other means of access. Further, cables often extend from the carts to walls providing additional obstruction. Once again, in medical applications, this impediment may be costly and/or life threatening.

In addition to obstructing access to medical equipment, such systems also provide very limited flexibility. That is, where the number of components varies or where components must be interchanged often, there is a need for an expandable system which provides easy access to the system components and relative ease in interchanging components.

SUMMARY OF THE INVENTION

In one embodiment, a wall-mountable medical monitoring system includes a center support rigidly mounted to a wall and projecting forwardly therefrom. Mounting to the wall is achieved using an extruded metal mounting plate which supports the center support and the power supply. The mounting plate is a longitudinal metal plate having a pair of tracks to which the center support and additional devices, such as power supplies, are mounted. Mounting flanges in the mounting plate slide within gaps in the tracks to attach the center support to the mounting plate with binding screws forcing the flanges into frictional engagement with the mounting plate. Detachable module housings are attached to the center support. Each module housing includes a substantially rectangular module chamber extending rearwardly from its front face toward the wall. A plurality of module guides within the module chamber define module slots into which modular components may slide.

The monitoring system also includes a plurality of modular components, each of which is shaped and sized for insertion into a respective module slot. A touch-screen display is mounted atop the center support with its rear face substantially adjacent the wall and its front face positioned for viewing by an observer. The display is attached to the center support by a pedestal which permits the display to pivot into two orthogonal directions. The rear face of the module housing is spaced apart from the wall, leaving a gap between the wall and the rear face of the module housing.

Low-profile components, such as power supplies, attach directly to the mounting plate beneath the center support.

A pair of secondary tracks on the mounting plate provide a passageway for cables to pass beneath the electronic device. A cable retainer retains the cables between the secondary tracks and prevents them from being tangled. The components communicate with the display through conventional cables which pass through cable slots in the rear face of the module chamber. The module housings are mounted to the center support using retainer brackets which project sidewardly from the center support member and engage the upper and lower surfaces of the module housing. Retainer nuts attach to the distal ends of the retainer brackets to hold the retainer brackets in place and prevent the module housing from detaching from the center support. The retainer nuts are easily detachable to permit replacement of the retainer brackets with extended retainer brackets which permit additional module housings to be mounted to the center support, thereby permitting additional components to be incorporated into the system.

Where additional space is needed for an electronic device within the module chamber, a center guide which divides the module housing into two segments may be removed to permit a double-size electronic device to be inserted into the module housing.

BRIEF DESCRIPTION OF THE DRAWINGS

FIG. 3 is a front elevational view of an embodiment of the mounting system including a third module housing.

DETAILED DESCRIPTION OF THE INVENTION

Figure 1:
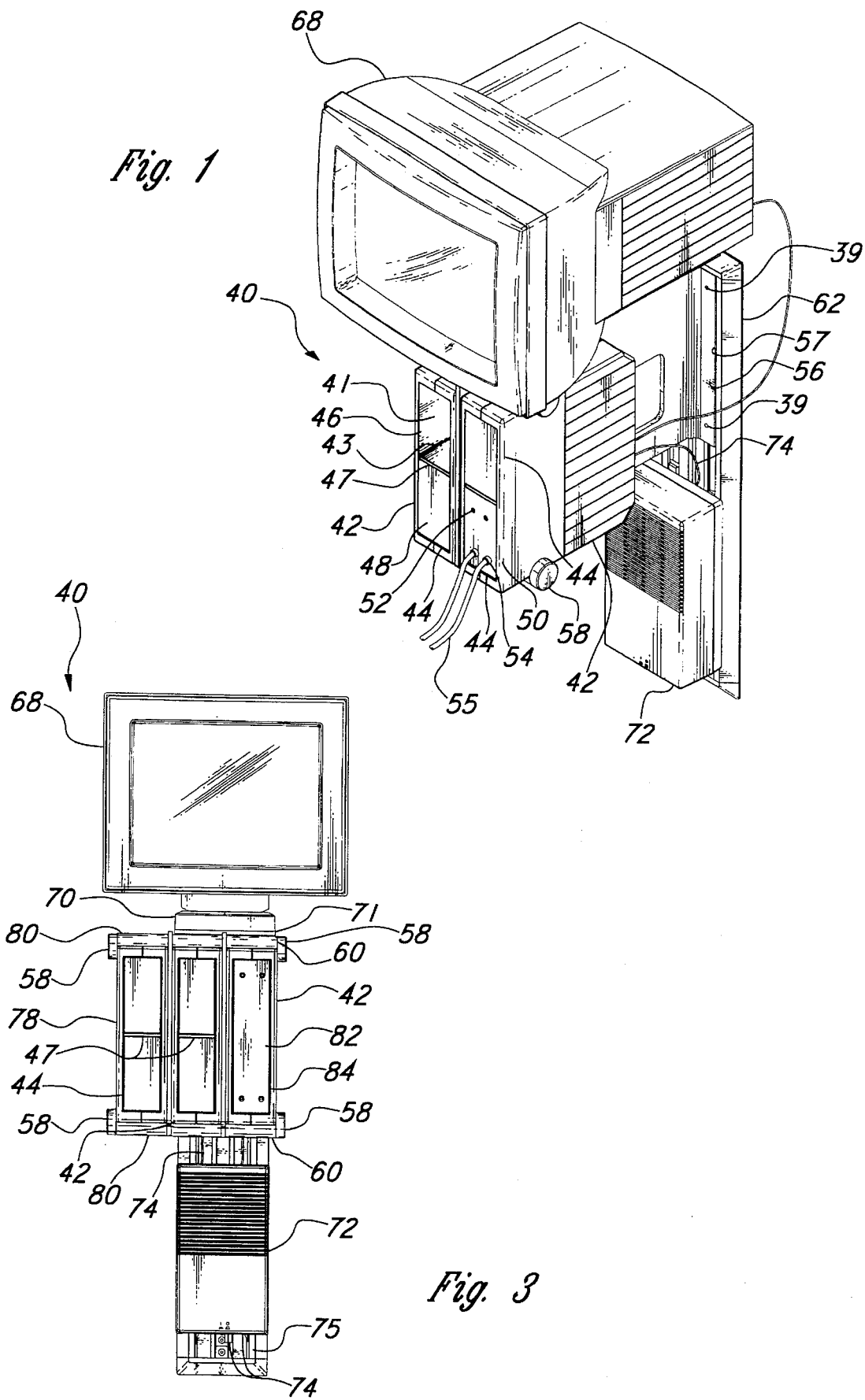
FIG. 1 is an isometric view of the preferred embodiment of the mounting system.

As shown in FIG. 1, a medical monitoring system 40 includes module housings 42 attached to a center support 56 mounted to a wall by a mounting plate 62. The module housings 42 include rectangular module chambers 41 having a detachable center guide 47 defining a pair of module slots 46 within each module chamber 41 (except for the rightmost module housing 42 of FIG. 3, discussed in greater detail below). Module guides 43 (visible in the empty module slot 46 in FIG. 1) extend rearwardly along the module slots 46.

Modular components 44 having generally rectangular cross sections slide into corresponding module slots 46 in the module housing 42 with a front face 48 of each of the components 44 exposed at a forward end 50 of the module housing 42. The module guides 43 (visible in the empty module slot 46 of FIG. 1) engage the components 44 to guide the components 44 into the module slots 46 and to provide mechanical support.

The components 44 may be of several different, interchangeable types, with particular types chosen for specific applications. For example, in some instances, a combination of monitoring components, such as heart monitors, electroencephalographs, and other medical monitors may be inserted in the respective module slots 46. As the need for particular types of components changes, the components 44 may be removed from the module slots 46 and replaced with alternative components, as appropriate. Because the front faces 48 of the components 44 are exposed and accessible, controls 52 and terminals 54 are incorporated into the components 44 and positioned to be accessible when the components 44 are in the module slots 46. To provide a means for monitoring a patient, cables 55 detachably connect to the components 44 using conventional couplers.

Figure 2:
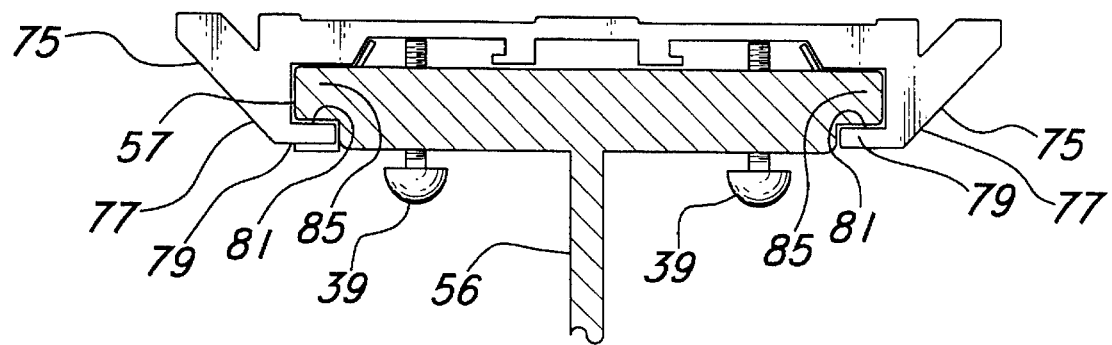
FIG. 2 is a cross-sectional detailed view of a portion of the mounting system of FIG. 1 showing the mounting flange engaging the tracks.
Figure 7:
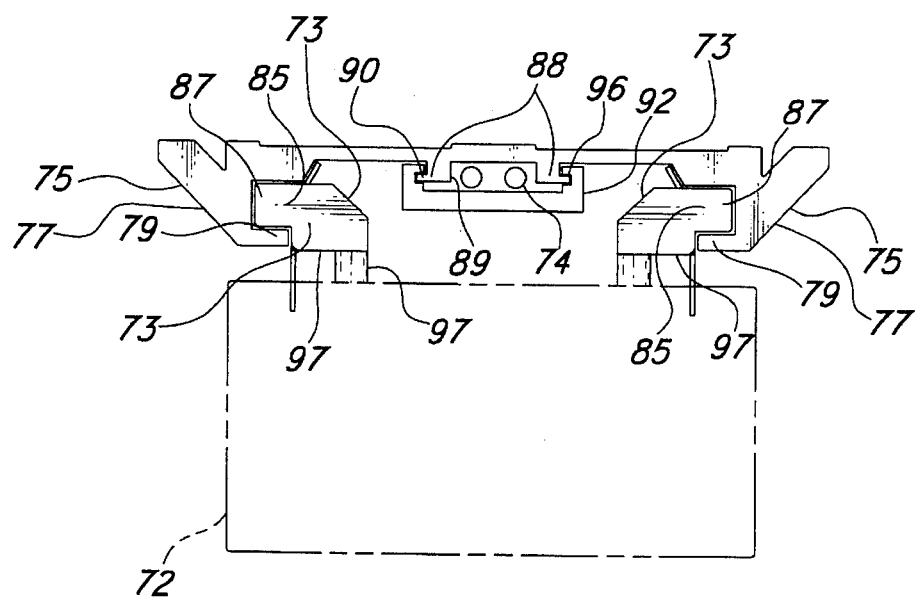
FIG. 7 is a cross-sectional detailed view of a portion of the mounting system of FIG. 1 with the power supply shown in phantom.

As discussed above, each of the module housings 42 attaches to the center support 56 which mounts in turn the mounting plate 62. The mounting plate 62 is a longitudinal, substantially planar structure, preferably formed from a single piece of metal, typically aluminum, using known techniques such as extrusion. As best seen in FIGS. 2 and 7, a pair of longitudinal tracks 75 integral to the mounting plate 62 project forwardly from the forward surface of the mounting plate 62. Each of the tracks 75 includes a forwardly extending leg 77 projecting from a forward surface of the mounting plate and a transversely extending leg 79 projecting from the forwardly extending leg 77. An inner surface 81 of the transversely extending leg 79 parallels the forward surface of the mounting plate, forming an elongated track gap 85 between the transversely extending leg 79 and the mounting plate 62.

The center support 56 is a rigid metal member having mounting flanges 57 extending sidewardly from its rearward end. The mounting flanges 57 extend sidewardly into the gaps 85 in the tracks 75 (best seen in FIG. 2) where they are prevented from moving away from the wall by the transverse legs 79 of the tracks 75. Binding screws 39 are threaded through holes in the mounting flanges and engage the forward surface of the mounting plate 62. As the binding screws 39 are tightened, they force the center support 56 away from the wall and force the outermost portions of the mounting flanges 57 into frictional engagement with the transverse legs 79. This frictional engagement provides support and retains the center support 56 in its rigidly mounted position.

Figure 4:
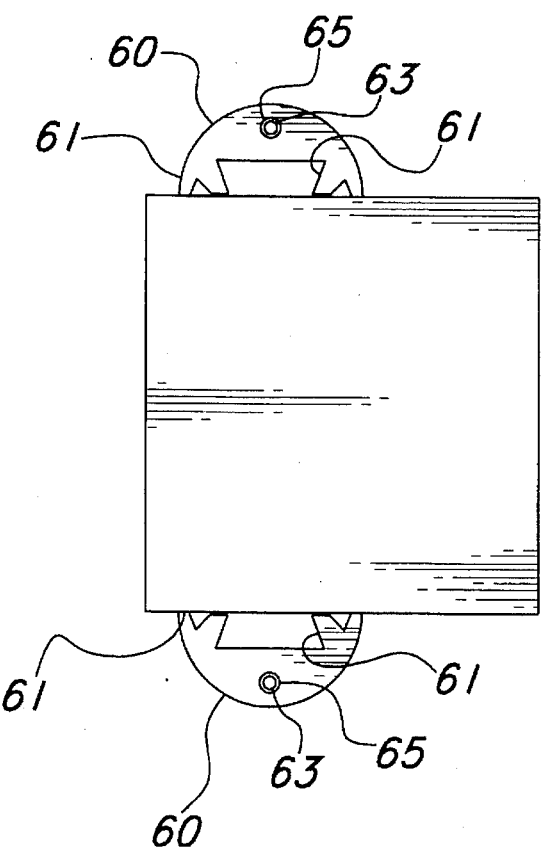
FIG. 4 is a side cross-sectional detailed view of a portion of the embodiment of FIG. 1 showing the module housings and retaining brackets.

A pair of longitudinal retainer brackets 60 (best seen in FIGS. 3 and 4) having a generally semicircular cross-section attach the module housings 42 to the center support 56. The retainer brackets 60 project sidewardly front the center support 56 and engage the upper and lower surfaces of the module housings 42 with integral fingers 61 formed in the retainer brackets 60. The retainer brackets 60 are slidably mounted to the center support 56 by retainer bolts 63 having female threading at a first end and a threaded extension at their second ends. The female threads at the first end of the retainer bolts thread onto threaded mounting bolts which project sidewardly from the center support 56. The retainer bolts 63 extend through passageways 65 in the retainer brackets 60. To retain the module housings 42 in place, retainer nuts (not shown) covered by respective caps 58 are threaded onto the threaded second ends of the retainer bolts 63. The retainer brackets 60 are positioned near a forward end of the center support 56, sufficiently far from the mounting plate 62 to provide a gap 64 (FIG. 5) between the mounting plate 62 and a rear face 66 of the module housings 42 when the module housings 42 are attached.

Figure 5:
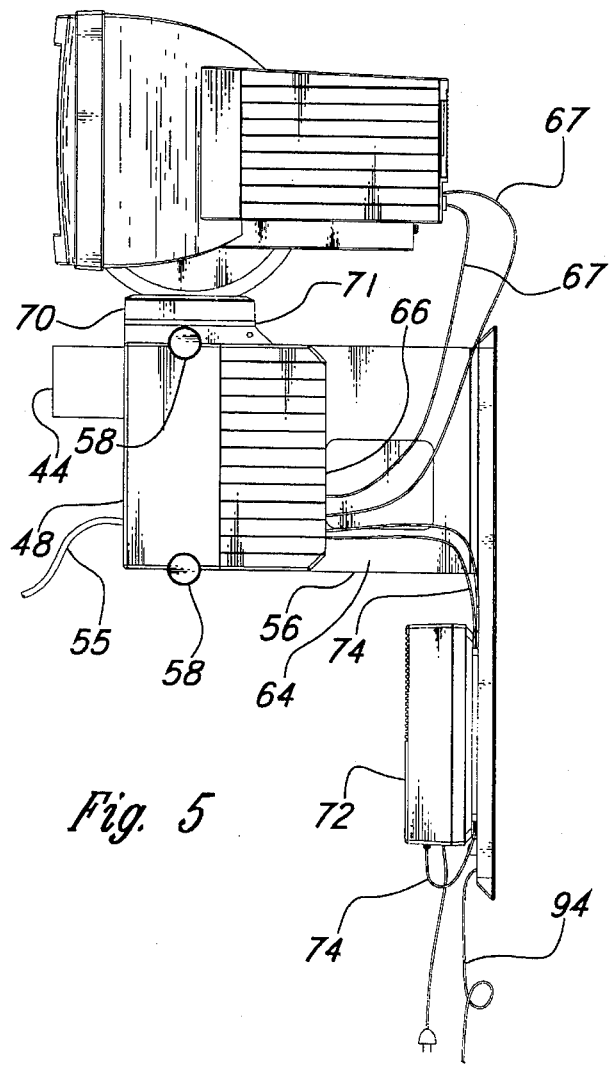
FIG. 5 is a side elevational view of the embodiment of FIG. 1.

In addition to supporting the module housings 42, the center support 56 also includes an integral platform 71 (FIGS. 3 and 5) for supporting a display 68 mounted to the platform 71 by a pedestal 70. The display 68 is a cathode ray tube (CRT) touch-screen assembly which pivotably attaches to the pedestal 70 which, in turn, bolts to the platform 71. The pedestal 70 advantageously permits the display 68 to be pivoted in two orthogonal directions for ease of viewing by a user. The display 68 is mounted with its touch-screen facing forwardly for ease of access and its rear face near the wall, as best seen in FIG. 5. In this position, the display 68 provides the minimum obstruction to the medical environment and permits the cables 67 to be kept near the wall minimizing any obstruction they may cause.

The front faces 48 (FIGS. 1 and 5) of the components 44 are substantially coplanar with, and slightly rearward of, the front face of the display 68 such that they provide minimal obstruction. However, because the front faces 48 are positioned near the plane of the front face of the display 68, they are easily accessible to a user.

Figure 6:
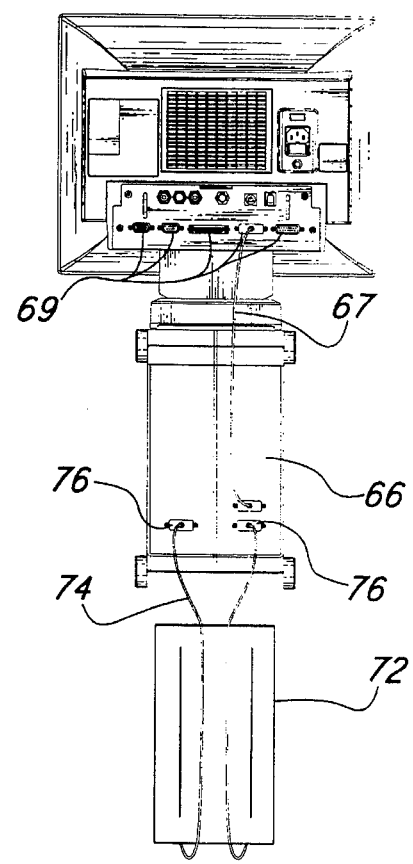
FIG. 6 is a rear elevational view of the embodiment of FIG. 1 with the mounting plate and a portion of the center support removed.

An additional electronic device, such as a low profile precision power supply 72 which supplies power for the components 44 is mounted to the mounting plate 62 beneath the center support 56. The power supply 72 is electrically connected to the components 44 through conventional cables 74 which reach the components 44 through conventional converters 76 mounted in the rear face 66 of the module housing 42, as best seen in FIG. 6. Because user access to the power supply 72 is rarely necessary, the power supply 72 is mounted beneath the module housings 42, adjacent the wall to provide a minimum of obstruction. It will be understood that, although the electronic device described herein is a single power supply 72, other or additional devices may also be included where appropriate for the specific medical application.

As shown in FIG. 7, the power supply 72 is detachably mounted to the mounting plate 62 by a pair of mounting brackets 73 which engage the tracks. The mounting brackets 73 include a substantially planar base portion 97 for mounting to the power supply 72 and a resilient mounting finger 87 extending forwardly and downwardly from the base portion. When the power supply 72 is mounted to the track 75, the mounting finger 87 of each of the mounting brackets 73 is inserted into the track gap 85 and engages the transversely extending leg 79. The weight of the power supply 72 causes pivotal torque on the mounting finger 87, causing it to dig into the lower surface of the transverse leg 79 and into the forward surface of the mounting plate 62. The frictional engagement of the mounting finger 87 to the transverse leg 79 and the mounting plate 62 holds the power supply 72 in place. An end cap 99 covers a lower surface of the lower end of the tracks 75 to provide a barrier to prevent the brackets 73 from exiting the track gap 85 at the lower end of the tracks 75.

A pair of secondary tracks 88 also projects forwardly from the mounting plate 62, intermediate the tracks 75. Each of the secondary tracks 88 includes a forwardly extending leg 89 and a sideward lip 90 for attachment of a cable retainer 92, as shown in FIG. 7. The cable retainer 92 is a flexible, C-shaped clip having retaining lips 96 at its outermost edges. The retaining lips 96 engage the sideward lips 90 of the secondary tracks 88 to retain cables 94 (FIGS. 1, 5 and 7) between the power supply 72 and the mounting plate 62. The cable retainer 92 is attached to the secondary tracks 88 by flexing its central member 98 to separate the retaining lips 96 and permit them to pass around the sidemost edges of the sideward lips 90. Then the central member 98 straightens, the retaining lips 96 move toward each other to a position between the sideward lips 90 of the secondary tracks, 88 and the forward surface of the mounting plate 62. When the cable retainer 92 is attached to the secondary tracks 88, the cable retainer 92 and the groove between the secondary tracks 88 form a passageway concealed from view by the power supply 72. The concealed passageway permits electrical and other cables 74 to reach the device without being visible while reducing tangling of the cables and other problems caused by freely hanging cables.

As best seen in FIGS. 5 and 6, additional cables 67 extend from connectors 76 on the rear face 66 of the module housing 42 to the display 68, where they are connected in conventional fashion to one of the connectors 69 on the rear surface of the display 68. The display 68 receives electronic signals from the components 44 and provides a visual display for a user. Because the display 68 is a touch-screen display, it also provides signals to the components 44 through the cables 67 in response to selections by a user.

As shown in FIG. 3, additional components 44 may be incorporated in the monitoring system through the addition of a secondary module housing 78 which mounts adjacent one of the original module housings 42, adding additional retainer brackets 80 to the distal ends of the original retainer brackets 60 to form a support of sufficient length to support both of the module housing 42 and the secondary module housing 78. The secondary module housing 78 is substantially identical to the module housings 42 and provides space for an additional pair of components 44. The additional retainer brackets 80 are identical to the original retainer brackets 60. When an additional retainer bracket 80 is used, the retainer bolt 63 must be extended to be of sufficient length to pass through the passageway 65 of the retainer bracket 80. To extend the retainer bolt 63, the female threaded end of a second retainer bolt 63 is screwed onto the threaded end of the original retainer bolt 63 to form a double-length retainer bolt.

In some applications, it is desirable to use a modular component 82 of larger dimensions than the typical components 44. FIG. 3 presents a large modular component 82 mounted within the rightmost module housing 42. This configuration is achieved by removing the detachable center guide 47 to create a module slot 84 which is twice the size of each of the original module slots 46. In this embodiment, the large modular component 82 is sized to slide within the double module slot formed by the combination of the upper and lower module slots 46.

While the embodiments described above present module housings 42 adapted to support either one or two components 44, module housings 42 supporting any number of components 44 are within the scope of the invention. For example, the module housings 42 described above may be segmented into three compartments to support three separate components 44. Similarly, although the embodiments presented above present only monitoring systems incorporating two or three module housings 42, systems incorporating any number of module housings may be within the scope of the invention. Where a relatively simple monitoring system 40 is used, it may be appropriate to attach only a single module housing 42 to the center support 56. Where a more complicated system is required, additional housings may be attached to the center support 56 or additional center supports may be attached to the mounting plate 62 above or below the original center support 56 to provide support for additional module housings 42. Moreover, while the mounting plate 62 is shown supporting only a single center support 56 and a single power supply 72, the mounting plate may be extended to support additional center supports and/or additional power supplies 72 or other components.

It will be appreciated that, although specific embodiments of the invention have been described herein for purposes of illustration, various modifications may be made without departing from the spirit and scope of the invention. Accordingly, the invention is limited except as by the appended claims.

I claim:

1. A medical monitoring system for use in a facility, comprising:

a center support having a first end rigidly mounted to a wall of the facility and having a second end projecting therefrom in a forward direction;

a display having a housing with a forward end and a rearward end, the display including a display screen at the forward end of the housing, the display mountable atop the center support with the rearward end substantially adjacent the wall and the display facing forwardly for viewing by an observer;

a module housing rigidly attached to the center support beneath the display at the forward end of the center support, the module housing having front and rear faces and four sidewalls, the four sidewalls defining a module chamber extending rearwardly from the front face of the module support housing toward the wall; and a plurality of modular components, each of the modular electronics device being sized for insertion into the module chamber.

2. The system of claim 1 wherein the module chamber includes a substantially rectangular cross section and a plurality of module guides within the module chamber, the module guides defining plurality of module slots, the module slots being substantially rectangular in cross section and extending rearwardly from the front surface of the module support housing, the module guides engaging and supporting the modular components when the modular components are inserted in the module chamber.

3. The system of claim 1 wherein the rear face of the module housing is spaced apart from the wall, forming a gap therebetween, further including:

an electronic device having a rear surface for mounting to a wall, and being sized to fit within the gap between the wall and the rear face of the module housing.

4. The system of claim 1 wherein at least one of the modular components includes an output terminal coupled to provide an image to the display element and wherein the display element provides display in response to an output signal from the output terminal.

5. The system of claim 4 wherein the display element is a touch-screen display.

6. The system of claim 1, further including:

a second module housing rigidly attached to the center support beneath the display and to a second side of the center support opposite the first module housing, the second module housing having four sidewalls defining a second module chamber extending rearwardly from a front surface of the second module housing, the second module chamber having a substantially rectangular cross section, the second module housing further having a plurality of module guides, the module guides defining a plurality of module slots, the module slots being substantially rectangular in cross section and extending rearwardly from the front surface of the second module support housing.

7. The system of claim 1, further including:

a second module housing rigidly attached to the first module housing beneath the display element and to a side of the first module housing opposite the center support, the second module housing having four sidewalls defining a second module chamber extending rearwardly from a front surface of the second module housing, the second module chamber having a substantially rectangular cross section, the second module housing further having a plurality of module guides, the module guides defining a plurality of module slots, the module slots being substantially rectangular in cross section and extending rearwardly from the front surface of the second module support housing.

8. The system of claim 1, further comprising:

a substantially planar mounting plate having a rear surface adapted for mounting to the wall with the rear surface facing the wall, a substantially planar forward surface, a pair of parallel tracks rigidly attached to the forward surface, wherein the electronic device detachably mounts to the tracks achieving the mounting to the wall thereby.

9. The system of claim 8 wherein each of the tracks is formed by a forwardly extending leg projecting from the forward surface of the wall plate and a transverse leg projecting from the forwardly extending leg, the tracks extending longitudinally in a substantially vertical direction whereby an elongated track gap is formed between each transversely extending leg and the wall plate, wherein the electronic device detachably connects to the tracks forming the detachable mounting of the electronic device to the tracks thereby.

10. The system of claim 9, further comprising:

a plurality of mounting brackets, each mounting bracket including:
(a) a base portion attached to the electronic device; and
(b) a resilient mounting finger extending forwardly and downwardly from its respective base portion when the mounting finger is inserted in the track gap, whereby pivotal movement of the base portion toward the plate causes the mounting fingers to frictionally engage the transverse leg and a portion of the forward surface, forming the detachable connection of the electronic device to the wall plate thereby.

11. A medical monitoring system mountable to a wall of a facility, comprising:

a substantially planar mounting plate having a rear surface adapted for mounting to the wall with the rear surface facing the wall, a substantially planar forward surface, a pair of parallel tracks rigidly attached to the forward surface, each of the tracks being formed by a forwardly extending leg projecting from the forward surface and a transverse leg projecting from the forwardly extending leg, the tracks extending longitudinally in a substantially vertical direction whereby an elongated track gap is formed between each transversely extending leg and the wall plate;

a plurality of mounting brackets, each mounting bracket including:
(a) a base for mounting to a medical instrument; and
(b) a resilient mounting finger extending forwardly and downwardly from its respective base portion when the mounting finger is inserted in the track gap, whereby pivotal movement of the base portion toward the plate causes the mounting fingers to frictionally engage the transverse leg and a portion of the forward surface;

a medical instrument attached to the base;

a center support rigidly mounted at a first end to the wall plate, and projecting forwardly from the forward surface toward a second end;

a display platform mounted atop the center support;

a display pivotably attached to an upper surface of the display platform;

a module housing rigidly attached to the center support beneath the display and to one side of the center support, the module housing having four sidewalls defining a module chamber extending rearwardly from a front surface of the module housing, the module chamber having a substantially rectangular cross section, the module housing further having a plurality of module guides, the module guides defining a plurality of module slots within the module chamber, the module slots being substantially rectangular in cross section and extending rearwardly from the front surface of the module housing; and a plurality of modular components, each electronic device being substantially rectangular in cross section and being sized for insertion into the module slots.

12. The system of claim 11, further including:

a pair of secondary tracks rigidly attached to the wall plate at the forward surface intermediate and parallel to the tracks, each of the secondary tracks including a secondary rail extending in a substantially vertical direction and projecting forwardly from the forward surface, each the secondary track further including a lip extending sidewardly from the secondary rail; and a cable retainer for attachment to the secondary rail, the cable retainer including a flexible, substantially planar central piece and a pair of retaining arms projecting orthogonally from opposite ends of the central piece, the retaining arms including a slot at their distal ends for engaging the lip.

13. The system of claim 12, further including:

a plurality of screw holes extending rearwardly though the plate from the forward surface; and a plurality of mounting holes through a portion of the center support, the mounting holes being alignable with the screw holes, to permit the center support to be bolted to the plate to form the rigid mounting thereto.

14. The system of claim 11, further including an end cap covering a lower surface of a lower end of the tracks, the end cap providing a barrier to prevent the brackets from exiting the gap at its lower end.

* * * * *